(12) United States Patent
Weiser

(10) Patent No.: US 7,981,136 B2
(45) Date of Patent: Jul. 19, 2011

(54) WOUND CLOSURE DEVICE

(76) Inventor: Leslie P. Weiser, Wellesley, MA (US)

( * ) Notice: Subject to any disclaimer, the term of this patent is extended or adjusted under 35 U.S.C. 154(b) by 497 days.

(21) Appl. No.: 11/953,632

(22) Filed: Dec. 10, 2007

(65) Prior Publication Data

US 2008/0228219 A1    Sep. 18, 2008

Related U.S. Application Data

(63) Continuation-in-part of application No. 10/884,837, filed on Jul. 2, 2004, now abandoned, which is a continuation-in-part of application No. 10/412,967, filed on Apr. 14, 2003, now abandoned.

(60) Provisional application No. 60/934,248, filed on Jun. 12, 2007, provisional application No. 60/873,643, filed on Dec. 8, 2006.

(51) Int. Cl.
*A61B 17/08* (2006.01)

(52) U.S. Cl. ............ 606/213; 606/215; 602/42; 602/57; 602/58

(58) Field of Classification Search .................. 606/213, 606/215; 602/52, 54, 57
See application file for complete search history.

(56) References Cited

U.S. PATENT DOCUMENTS

| | | |
|---|---|---|
| 1,074,413 A | 9/1913 | DeBaun et al. |
| 1,230,444 A | 6/1917 | Teed |
| 2,196,296 A | 4/1940 | Flynn |
| 2,751,909 A | 6/1956 | Weitzner |
| 3,528,426 A | 9/1970 | Vukojevic |
| 3,971,384 A | 7/1976 | Hasson |
| 4,423,731 A | 1/1984 | Roomi |
| 4,526,173 A | 7/1985 | Sheehan |
| 4,531,521 A | 7/1985 | Haverstock |
| 4,561,435 A * | 12/1985 | McKnight et al. ............... 602/42 |
| 4,655,209 A | 4/1987 | Scott |
| 4,950,282 A | 8/1990 | Beisant et al. |
| 5,176,703 A | 1/1993 | Peterson |
| 5,234,462 A | 8/1993 | Pavletic |
| 5,263,970 A | 11/1993 | Preller |
| 5,336,219 A | 8/1994 | Krantz |
| 5,415,626 A | 5/1995 | Goodman et al. |

(Continued)

FOREIGN PATENT DOCUMENTS

CA    2499866    1/2006

(Continued)

OTHER PUBLICATIONS

International Search Report dated Dec. 23, 2005, received in PCT/US05/23362.

(Continued)

*Primary Examiner* — Darwin P Erezo
(74) *Attorney, Agent, or Firm* — Jacob N. Erlich, Esq.; Burns & Levinson, LLP; Yakov Korkhin, Esq.

(57) ABSTRACT

The present development includes an elongated flexible base strip having its bottom surface coated with an adhesive material suitable for adherence to skin and constructed with bridging links spaced along the inner edge of the base strip and extending outwardly therefrom. The inner edge of the base strip is intended to be aligned adjacent to a lip of the wound being treated. Each of the bridging links has an adhesive coated section displaced from the inner edge. In the packaged or stored position, prior to engagement, the bridging links are folded over the upper surface of the adhesive strip about a hinge that is at the joint of the bridging link to the base strip.

19 Claims, 12 Drawing Sheets

U.S. PATENT DOCUMENTS

| | | |
|---|---|---|
| 5,497,788 A | 3/1996 | Inman et al. |
| D371,604 S | 7/1996 | Savage et al. |
| 5,534,010 A | 7/1996 | Peterson |
| 5,562,705 A | 10/1996 | Whiteford |
| 5,630,430 A | 5/1997 | Shultz et al. |
| 5,733,308 A | 3/1998 | Daugherty et al. |
| 5,779,659 A | 7/1998 | Allen |
| D401,339 S | 11/1998 | Chambers |
| 5,843,025 A | 12/1998 | Shaari |
| 5,891,077 A | 4/1999 | Gilman et al. |
| 5,947,998 A | 9/1999 | Cartmell et al. |
| 6,007,564 A | 12/1999 | Haverstock |
| 6,043,406 A | 3/2000 | Sessions et al. |
| 6,093,465 A | 7/2000 | Gilchrist et al. |
| 6,176,868 B1 | 1/2001 | Detour |
| 6,293,281 B1 | 9/2001 | Shultz et al. |
| 6,329,564 B1 | 12/2001 | Lebner |
| 6,425,876 B1 | 7/2002 | Frangi et al. |
| 6,468,383 B2 | 10/2002 | Kundel |
| 6,495,230 B1 | 12/2002 | do Canto |
| 6,822,133 B2 | 11/2004 | Lebner |
| 6,831,205 B2 | 12/2004 | Lebner |
| 6,942,683 B2 | 9/2005 | Dunshee |
| 7,022,891 B2 | 4/2006 | Beaudry |
| 7,066,182 B1 | 6/2006 | Dunshee |
| 7,067,710 B1 | 6/2006 | Beaudry |
| 7,074,982 B2 | 7/2006 | Knutson et al. |
| 7,122,712 B2 | 10/2006 | Lutri et al. |
| 7,186,878 B2 | 3/2007 | Beaudry |
| 7,232,454 B2 | 6/2007 | Rousseau |
| 7,267,681 B2 | 9/2007 | Dunshee |
| 7,332,641 B2 | 2/2008 | Lebner et al. |
| 7,354,446 B2 | 4/2008 | Lebner |
| 7,414,168 B2 | 8/2008 | Lebner |
| 7,511,185 B2 | 3/2009 | Lebner |
| 7,696,399 B2 | 4/2010 | Rogers |
| 2002/0099315 A1 | 7/2002 | Lebner |
| 2004/0204740 A1 | 10/2004 | Weiser |
| 2004/0243040 A1 | 12/2004 | Weiser |
| 2005/0020957 A1 | 1/2005 | Lebner |
| 2005/0021081 A1 | 1/2005 | Lebner |
| 2005/0021083 A1 | 1/2005 | Lebner |
| 2006/0142686 A1 | 6/2006 | Morse |
| 2007/0038246 A1 | 2/2007 | Lebner et al. |
| 2007/0038247 A1 | 2/2007 | Lebner et al. |
| 2007/0191752 A1 | 8/2007 | Lebner |
| 2008/0114396 A1 | 5/2008 | Cory et al. |
| 2008/0154168 A1 | 6/2008 | Lutri |
| 2008/0262540 A1 | 10/2008 | Bangera et al. |
| 2009/0240186 A1 | 9/2009 | Fang |

FOREIGN PATENT DOCUMENTS

| | | |
|---|---|---|
| WO | WO/2006/014323 | 2/2006 |
| WO | 2006040379 A1 | 4/2006 |

OTHER PUBLICATIONS

Written Opinion of the International Searching Authority dated Dec. 23, 2005, received in PCT/US05/23362.

International Preliminary Report on Patentability dated May 17, 2006, received in PCT/US05/23362.

International Search Report dated Jul. 13, 2009, received in PCT/US2008/086217.

* cited by examiner

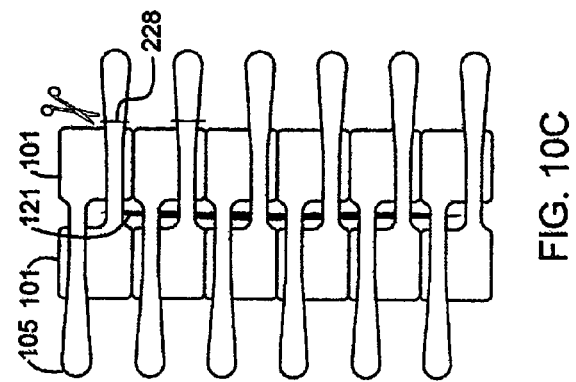
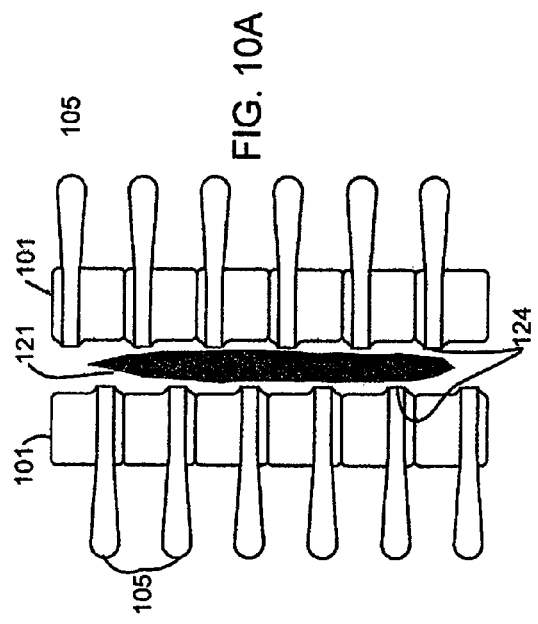
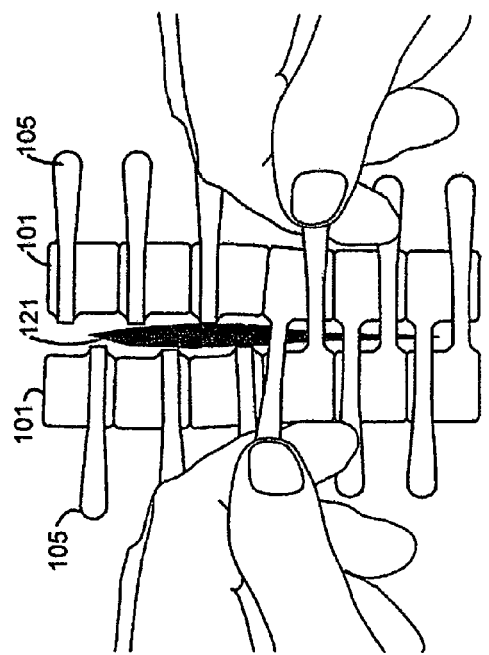

WOUND CLOSURE DEVICE

CROSS-REFERENCE TO RELATED APPLICATIONS

The present application claims priority, as a continuation-in-part type application, under 35 U.S.C. §120 to U.S. patent application Ser. No. 10/884,837, filed Jul. 2, 2004, now abandoned, which is a continuation-in-part application of U.S. patent application Ser. No. 10/412,967, filed Apr. 14, 2003, now abandoned, and claims priority therefrom with respect to common subject matter.

The present application also claims the priority benefit under 35 U.S.C. §119(e) of U.S. Provisional Application Ser. No. 60/934,248, filed Jun. 12, 2007, and U.S. Provisional Application Ser. No. 60/873,643, filed Dec. 8, 2006.

The entire contents of each of the aforementioned provisional and nonprovisional applications are incorporated herein by reference.

The present application also claims the priority benefit under 35 U.S.C. §119(e) of U.S. Provisional Application Ser. No. 60/934,248, filed Jun. 12, 2007, and U.S. Provisional Application Ser. No. 60/873,643, filed Dec. 8, 2006.

The entire contents of each of the aforementioned provisional and nonprovisional applications are incorporated herein by reference.

BACKGROUND

The disclosure of this application relates to wound closure devices. Among the most common methods for closing wounds caused by lacerations or surgical incisions are suturing and stapling. Both of these procedures are skin invasive, which can traumatize and compromise the integrity of the wound. They increase the possibility of infection, expose the surgeon, as well as the patient, to blood-borne disease, leave behind scar tracks, and require a follow-up visit for suture or staple removal.

As is well known, a cut that invades deeply into the tissue of the skin generally requires a mechanism for drawing the sides of a wound together to promote healing and to reduce the formation of scar tissue. Surgeons have become skilled in the various techniques of suturing to minimize the resulting blemish that occurs during the healing process. These methods have always generated issues of sterilization and the very nature of suturing requires a threshold of dexterity that escapes many care providers. This is particularly true in emergency situations, which call for immediate treatment to secure the wound for transport or until such time as proper surgery is available. Suturing, even by a skilled surgeon, punctures and stresses skin tissue causing scaring.

It is well recognized that a sutureless wound closure would be a great benefit in many situations. Accordingly, the present disclosure provides an improved sutureless wound closure device which overcomes the above problems and others.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 10A-10C illustrate the steps of completing the closure of a wound with opposing base strips.

DETAILED DESCRIPTION OF THE PREFERRED EMBODIMENTS

Although the present invention will be described with reference to the embodiments shown in the figures, it should be understood that the present invention may have many alternate forms.

This application involves single component wound closures of the type described in U.S. patent application Ser. No. 10/884,837, filed Jul. 2, 2004, Ser. No. 10/412,967, filed Apr. 14, 2003, and provisional Application Nos. 60/873,643, filed Dec. 8, 2006, and 60/934,248, filed Jun. 12, 2007, all owned in common with the subject application. The entire disclosures of the cited applications are incorporated herein by reference. Although the product described in this application is illustrated primarily with reference to the above-cited wound closures, it may be used with a wide variety of products having similar application.

In the course of describing the wound closure embodiments herein, the bottom of the closing device will refer to the surface that is intended to engage the skin and the upper side or top will refer to the side of a component that is facing away from the skin after application. Directions will be indicated according to the position of the wound being treated, for example, transverse shall refer to directions across the wound. The inner edge of the closing device shall refer to the side that is intended to be adjacent to the wound lip, and the outer edge shall refer to the side of the device that is intended to be away from the wound.

Figure 1:
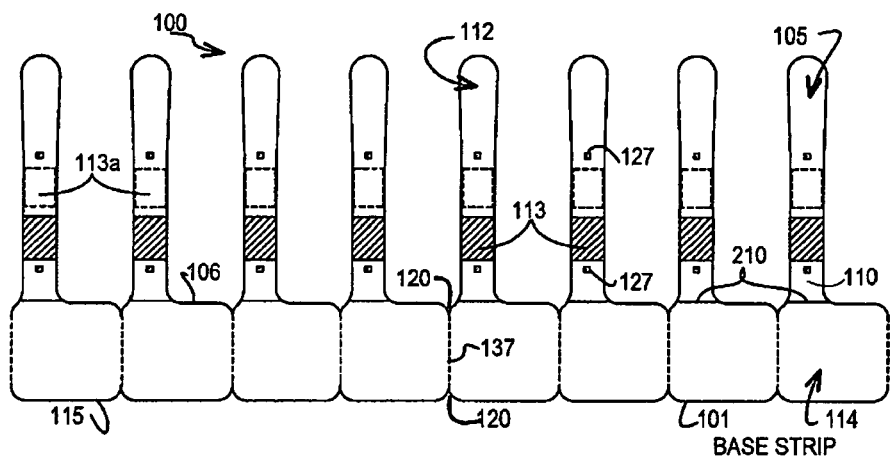
FIG. 1 is a top plan view of an exemplary embodiment wound closure of this disclosure.

As shown in FIG. 1, a wound closure device 100 is constructed for application to one or both sides of a wound to be closed. The wound closure device 100 is constructed having a base strip 101. The base strip 101 is constructed with bridging links 105, extending transversely outward with respect to the longitudinal axis of the base strip 101, from its inner edge 106. The bridging links 105 are connected to the base strip 101 by a hinge portion 110. The hinge portion 110 may include a fold line 210 which may be aligned with the inner edge 106, or, more preferably, as shown in FIG. 1, displaced therefrom. As described in greater detail below, when the fold line 210 is offset from the inner edge 106 in accordance with a preferred embodiment herein, the hinge regions 110 defines a tabs 124 (see FIG. 4), which may be used to separate the closure strip 100 from a protective backing sheet and/or to gauge a distance between the inner edge 106 and the edge of a wound to be closed.

In use, a length L (see FIG. 9A) of the base strip 101 may be cut from an elongated strip or roll (not shown), the length L being commensurate with the size of the wound to be closed. The device 100 is preferably formed of a flexible, fabric or fabric-like material. Most preferably, the device 100 is formed of a non-woven conformable fabric, such as ORION® fabric available from Cerex Advanced Fabrics, Inc. of Cantonment, Fla. The use of a conformable material for the base strip 101 allows the device to conform to shape of the wound to be closed.

Figure 2:
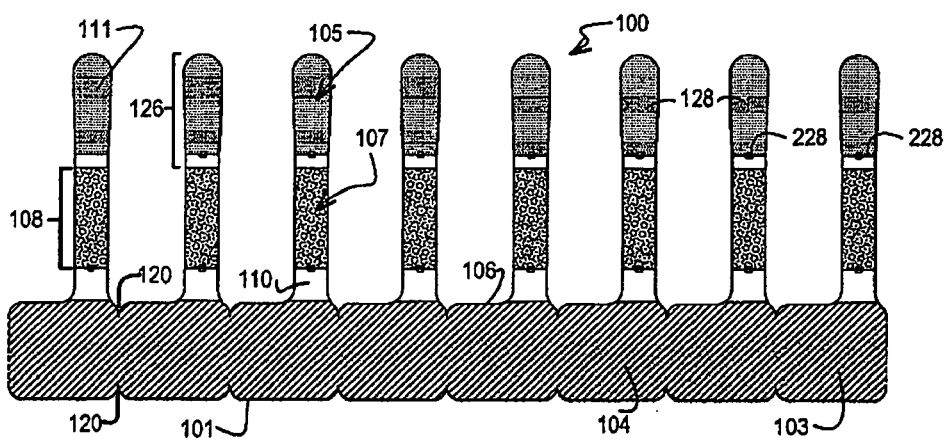
FIG. 2 is a bottom plan view of the wound closure device of FIG. 1.
Figure 3A:
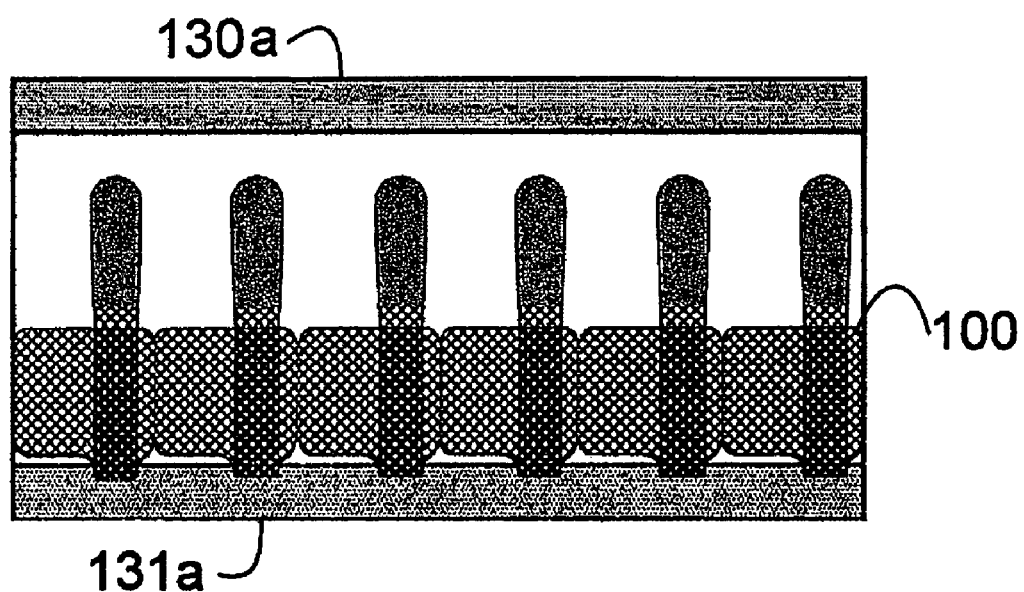
FIG. 3A is a plan view of the wound closure device appearing in FIG. 1 in a first packaged configuration.
Figure 3B:
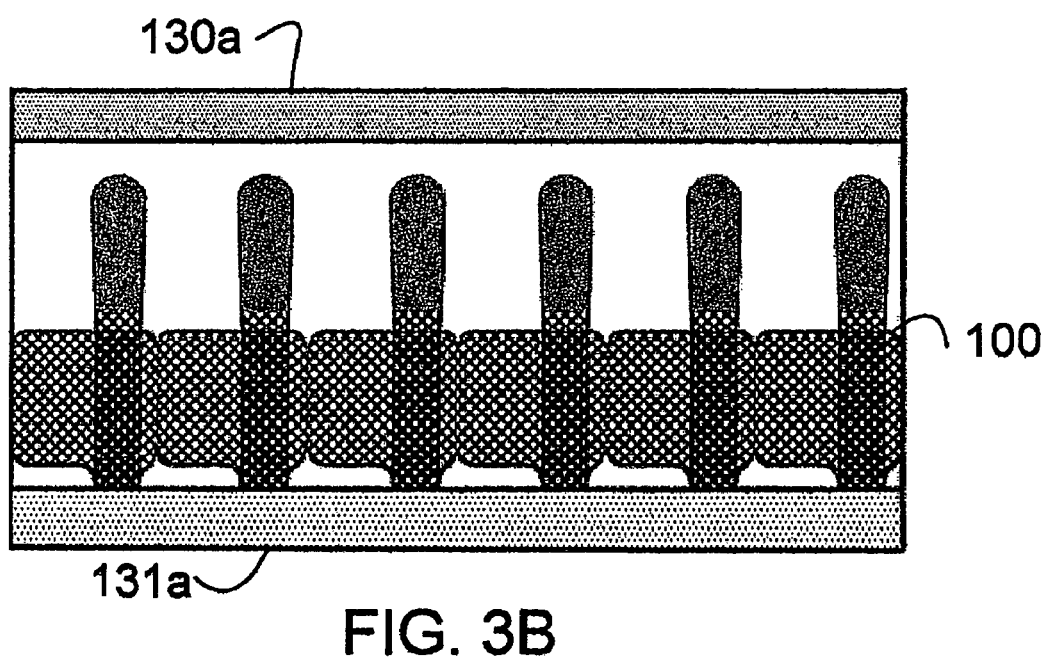
FIG. 3B is a plan view of a variation of the FIG. 3A embodiment, wherein the hinge tabs do not protrude over the edge strip.

As shown in FIGS. 1 and 2, the base strip 101 is coated with an aggressive, skin-compatible adhesive 103 on its bottom surface 104. A like or similar adhesive is coated on the bottom surface 107 of each of the bridging links 105 within an adhesive zone or region 108 thereof Except as indicated, the remaining area of the bottom surface 107 of the bridging links 105 is free of adhesive, in particular at hinge 110 and distal end 111. The upper surface 112 of each bridging link 105 is provided with a limited zone 113 of light tack adhesive to releasably hold the bridging link 105 in a folded position for packaging and to facilitate application to the wound, as shown in FIGS. 3A, 3B. As an alternative, the zone 113 may be provided with a co-adhesive that engages a similar and aligned zone of co-adhesive (not shown) on the upper surface 114 of the base strip 101.

Alternatively, the light tack adhesive may be placed in regions 113*a* (shown in broken lines) on the bridging links 105. Preferably, the light tack adhesive is placed in regions 113*a* when used with a non-folded upper release sheet 130*a* (see, e.g., FIG. 4) and in regions 113 when a folded upper release sheet 130*b* (see, e.g., FIG. 5) is used.

In the embodiment shown in FIG. 1, the base strip 101 is constructed with notches 120 aligned and spaced along the inner edge 106 and outer edge 115 of the base strip 101 to provide a transverse guide for proper cutting of the base strip 101 into lengths compatible with a wound 121. The notches 120 are located to encourage proper spacing of the cuts to facilitate offset placement of a pair of base strips to opposite sides of the wound. The notches 120 are formed in a rounded or chamfered shape to avoid pointed edges and promote adhesion after application.

As best seen in FIG. 1, the notches 120 are not centered between adjacent bridging links 105, but are axially offset from such a centered position. By offsetting the notches in this manner, the bridging links of said wound closure device will be axially offset from the bridging links of a like wound closure device positioned in facing relation on the opposite side of a wound. The position of the notches 120 (and optional guidelines 137, if provided) may be determined in the manner disclosed in commonly owned U.S. Patent Application Publication No. 2004/0243040, published Dec. 2, 2004, and incorporated herein by reference, for determining the position of guidelines. See, e.g., U.S. Patent Application Publication No. 2004/0243040 at page 5, numbered paragraphs 0064-0066.

In another embodiment, the bridging links 105 are provided with defined areas 108 of aggressive adhesive on the bottom surface 107 of each link 105. The defined areas 108 may be marked on the upper surface 112 of each link 105 by dots 127, or other appropriate indications, so that the adhesive zone 108 may be readily identified as the bridging link is applied across the wound and adhesive zone 108 thereby hidden.

Figure 9C:
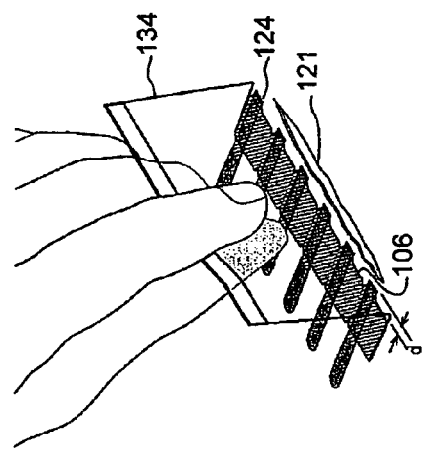
FIGS. 9A-9C illustrate the steps of applying the wound closure device of FIG. 1 to a wound.

In certain embodiments, the non-adhesive hinge section 110 is constructed to be folded along a hinge line 210 that is displaced from the inner edge 106 of the base strip 101. As best shown in FIG. 9C, a tab portion 124 is thus formed, extending outward from the inner edge 106 towards the wound 121. The tabs 124 may be used as a gauge to maintain an appropriate distance d between the inner edge 106 of the base strip 101 and the wound 121. The tab 124 may also act as a means to grasp the base strip 101, when a protective tape is being removed from the bottom surface 107 of the base strip 101 before application. Since in such embodiments, the hinge region 110 is free of adhesive, it may readily be grasped if necessary or desired to remove the closure strip 100 from the protective sheet. The tab 124 also assists in alignment of a pair of base strip lengths to opposite sides of the wound.

In another embodiment, as shown in FIG. 2, the distal end 111 of each bridging link 105 is provided with a non-adhesive zone 126, on which is layered one or more an additional film layers 128, e.g., to stiffen the outer end and facilitate grasping the bridging link 105 for engagement across the wound 121. The stiffening layer(s) provide additional control for precise wound closure, particularly where the closure device is formed of a relatively light weight material. The additional one or more layers may be laminated on the engaging side of the bridging links, the opposite side, or both. The film 128 may be constructed from a rayon micropore tape or the like and may be colored or textured to assist in visualizing and identifying the end of the bridging link.

The one or more additional layers of material 128 extend from the distal end of the bridging links toward the inner edge 106 and in a preferred embodiment the terminus of the stiffening layers 128 defines or corresponds to a preferential cut line 228 of the bridging link. These preferential cut lines 228 provide an indication of a recommended or convenient location for trimming the ends of a bridging link 105 after application, if necessary or desired. In embodiments wherein a stiffening layer is not provided, preferential cut lines 228 may be printed or marked on the bridging links. In embodiments wherein a stiffening layer is provided, preferential cut lines 228 may be printed or marked on the bridging links, although more preferably such marking or printing is omitted and the edge of the one or more stiffening layers defines the preferential cut line.

Advantageously, the stiffening film material may be formed of MICROPORE brand tape available from 3M. The use of a colored tape sets the pull tabs apart from the rest of the device and helps identify the distal ends of the bridging links as pull tabs. Where the stiffening layer(s) 128 are configured to terminate at a preferential cut line, the use of a contrasting or colored tape as the stiffening material helps in identifying and/or visualizing the cut lines. The tabs 124 may also have an intuitive shape to help identify them as a pull tabs.

Figure 4:
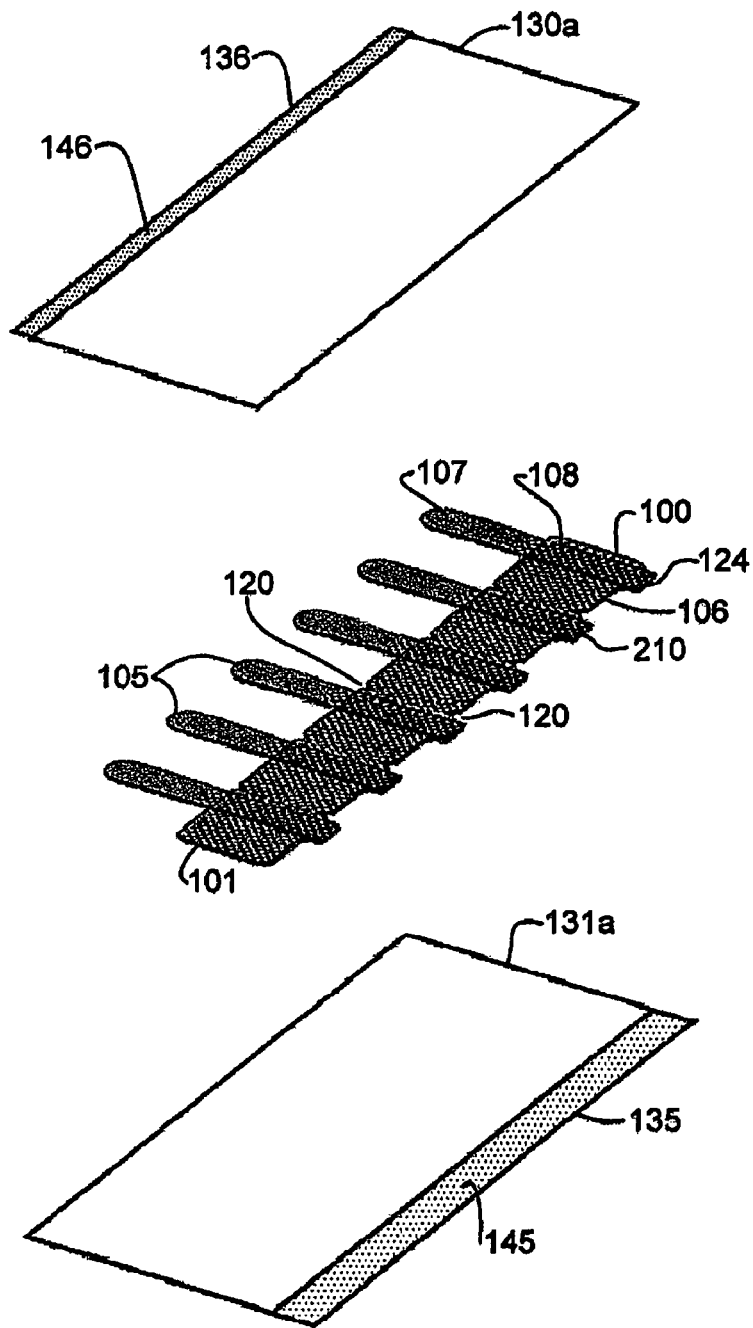
FIG. 4 is an exploded perspective view of the embodiments appearing in FIGS. 3A and 3B.

In one embodiment as shown in FIGS. 3A, 3B, and 4, upper and lower protective tapes 130*a* and 131*a*, respectively, are constructed to engage the exposed adhesive during storage and handling prior to application. The upper surface (in the orientation shown in FIG. 4) of lower protective tape 131*a* is treated with a release agent to removably engage the bottom surface 104 of the base strip 101 coated with the adhesive 103. When the bridging links 105 are in the stored, folded back position, the bottom surfaces 107 and adhesive zones 108 face upwardly. The lower surface of the upper protective tape 130*a* is treated with a release agent to removably engage the adhesive regions 108. It will be recognized that the assemblies shown in FIGS. 3A-8, comprising the closure strips and protective sheets, may be further packaged within a sterile, sealed envelop or other outer covering for storage and handling prior to use, as would be understood by persons skilled in the art.

The protective tapes 130a and 131a are constructed for sequential removal prior to application. The protective tapes 130a and 131a are preferably constructed of an optically clear plastic film having one side coated with a release agent, such as a silicone-based release material or the like, and the opposite side suitable for printing. The upper protective tape 130a is formed of a generally planar sheet of material.

The distal edge 136 of the upper protective tape 130a may be printed with indicia 146, which may be a color, texture, textual indicia, or other code to provide a notice to the user of the order of protective tape removal. For example, the indicia 146 may be a strip of colored material laminated along the distal edge 136 on the upper surface of the upper protective tape 130a.

The lower protective tape 131a is constructed in a size larger than the adhesive 103 covered bottom surface 104 of the base strip 101. Sufficient overlap may be constructed at one edge 135 to provide a means to grab the bottom protective tape 131a for removal.

The edge 135 of the bottom protective tape 131a may likewise be coded by indicia 145, such as color, textual indicia, texture, or other means to indicate to the user the order of protective tape removal. In a preferred aspect, the indicium 145 is a red strip printed or laminated along the distal edge 135 to symbolize the wound and the relative placement of the strip thereto.

A colored edge 135 is advantageous in that it effectively provides a visual profile for the tab 124, so that it may be readily identified and grasped. This provides an alternative means for removing the bottom protective tape 131a. Optionally, guidelines 137 (see FIG. 1) may be printed on the upper surface 114 of the base strip 101 to facilitate cutting of the base strip 101 in locations that facilitate alignment with an oppositely positioned length of base strip 101. Alternatively, the optional guidelines may be printed on the upper protective sheet 130a. In an especially preferred embodiment, the guidelines 137, where provided and whether printed on the section 133 and/or the base strip 101, extend transversely between each notch 120 in the inner edge 106 of the base strip 101 and the corresponding axially-aligned notch 120 on the outer edge 115 of the base strip 101. The guidelines 137, if printed on the base strip, may also be aligned to ensure that the bridging links 105 of base strip sections 101 applied to opposite sides of a wound to be closed are in offset or staggered relation as described in more detail below. Alternately, the guidelines are omitted and the notches 120 instead are used as a cutting guide.

In the embodiment of FIG. 3A, the hinge tabs 124 protrude onto or overlap with the colored strip 145. Advantageously, a red strip 145 or other indicia which visually contrasts with the material forming the closure device 100 (e.g., white) may assist the user in grasping the tab 124 for removal of the lower tape 131a. Alternatively, the fold line of the hinge tabs 124 may be aligned with the indicia strip 145, as shown in FIG. 3B.

Figure 5:
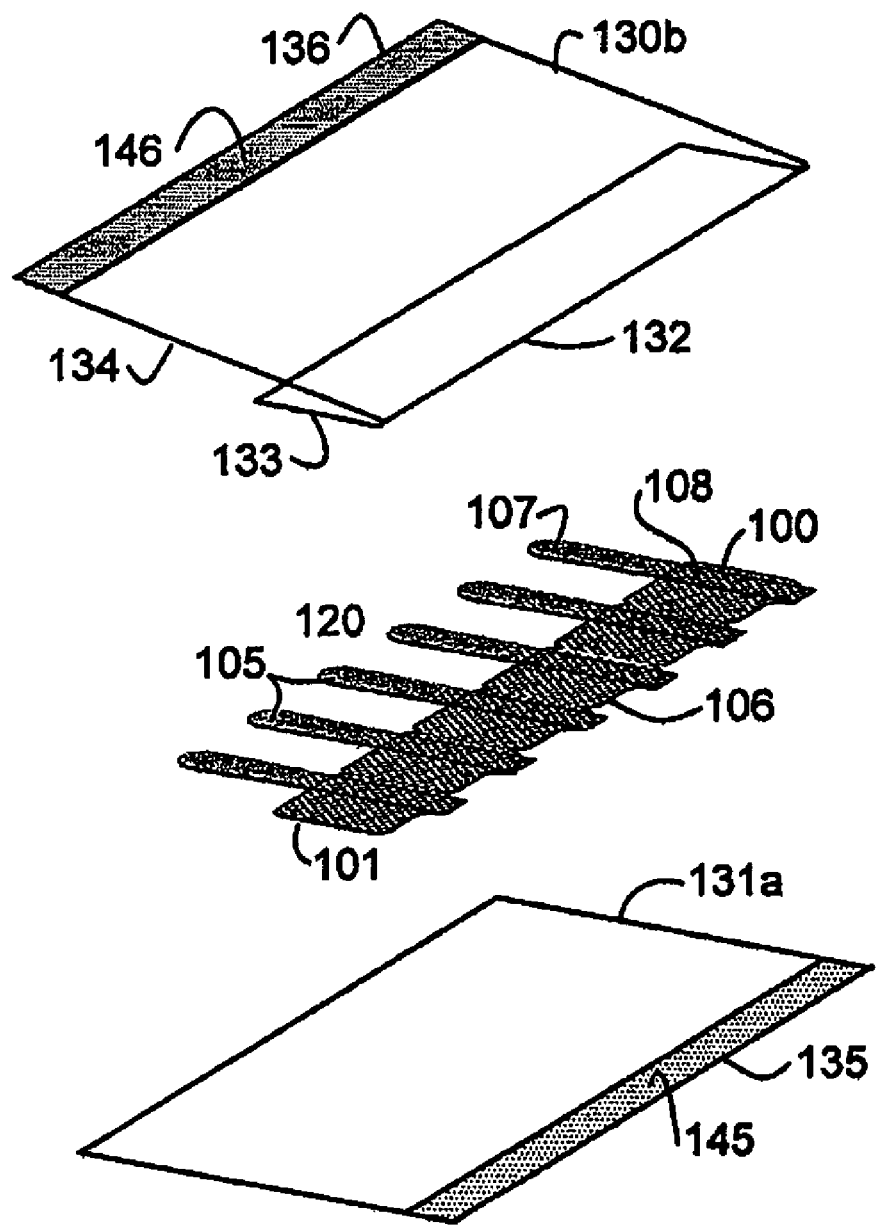
FIG. 5 is an exploded perspective view of a second packaged closure configuration.

The alternative embodiment appearing FIG. 5 includes an upper protective tape 130b in place of the upper protective tape 130a. The device appearing in FIG. 5 is as described above, except the tape 130b is folded along a longitudinally-extending axis 132 to provide an adhesive engaging section 133 and an outwardly extending flap portion 134. The flap portion 134 may be used to grasp the protective tape and base strip and is preferably sized to provide ample surface for convenient holding. The adhesive-engaging section 133 of the upper protective tape 130b is shaped to engage and cover the adhesive zones 108 of the bridging links 105.

In a preferred embodiment, especially in the case of a folded upper protective sheet 130b of FIG. 5, the release agents on the upper and lower protective tapes are chosen having different release factors so that the bottom protective tape 131a is more easy to remove than upper protective tape 130b. Thus, the releasable bond between the upper protective tape 130b and the adhesive regions 108 has a greater tack or tenacity than the releasable bond between the bottom protective tape 131a and the bottom surface 104. Removal of the tape 131a, accordingly, takes less force than it takes to remove the tape 130b. In this manner, the upper sheet 130b may be held, e.g., by portion 134, and the closure 100 will remain adhered to the upper sheet as the lower protective tape 131a is removed. In this manner, the lower protective tape 131a may be stripped from the base strip 101, which remains attached to the upper protective tape 130b for placement of the wound closure device 100 adjacent to the wound 121. Since the upper sheet 130b remains in place, it may then be used as a holding means or handle for applying the wound closure device 100 to a straight or curved wound.

In the case of the non-folded upper protective tape 130a, the release factor may be the same as or different than the release factor for the lower sheet 131a. While the differential release factors as described above by way of reference to FIG. 5 may also be employed with the FIG. 4 embodiment, it is preferred that, in the case of a non-folded sheet 130a, the release factor for the upper sheet 130a is the same as the release factor for the lower sheet 131a.

Figure 6A:
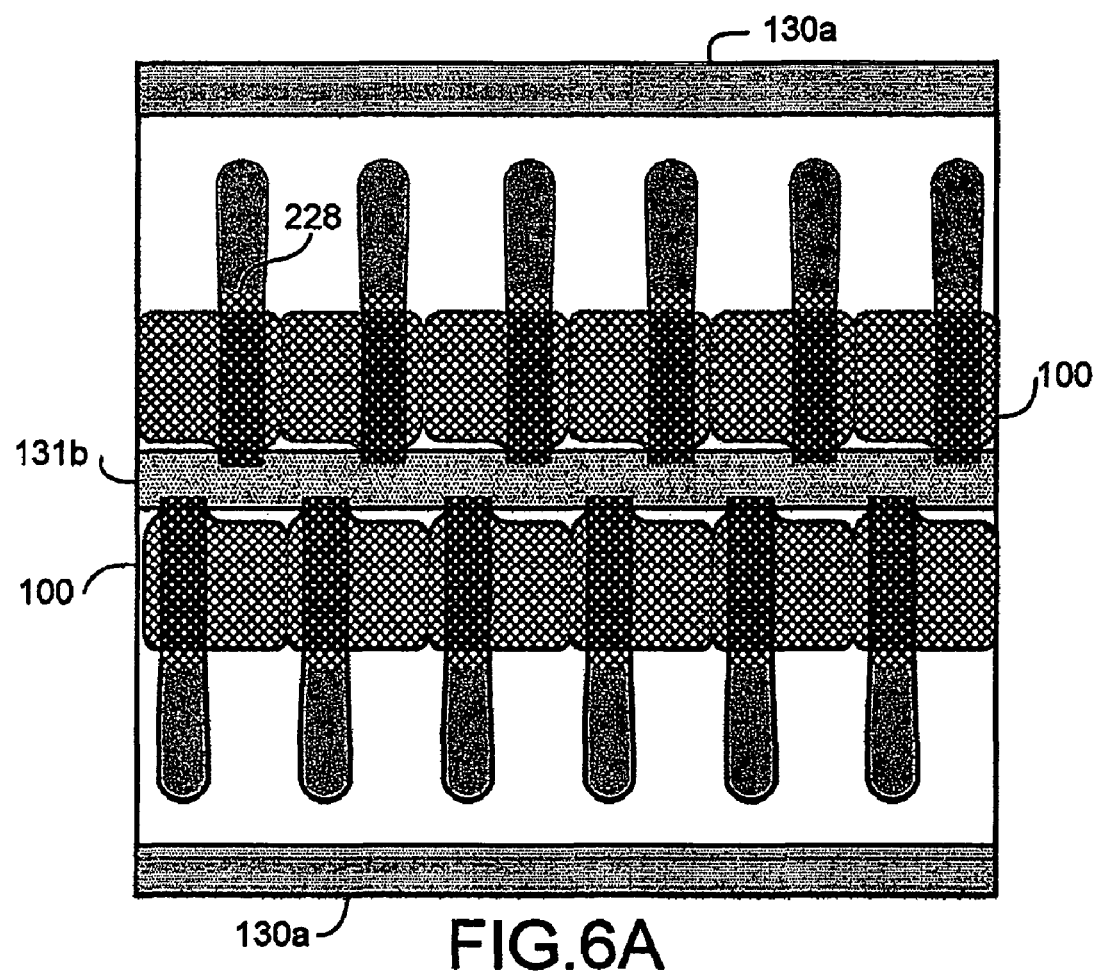
FIG. 6A is a plan view of a third packaged closure configuration.
Figure 6B:
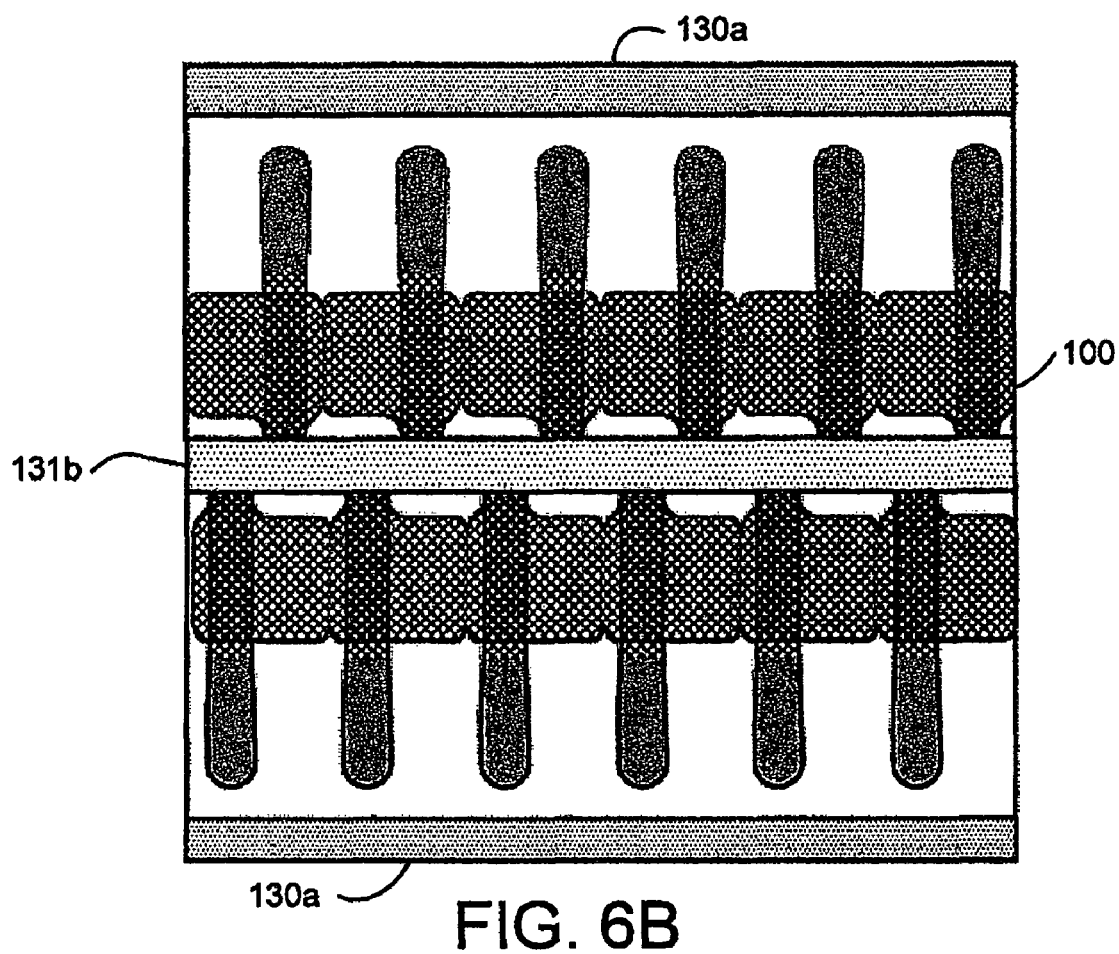
FIG. 6B is a plan view of a variation of the FIG. 6A embodiment, wherein the hinge tabs do not protrude over the edge strip.
Figure 7:
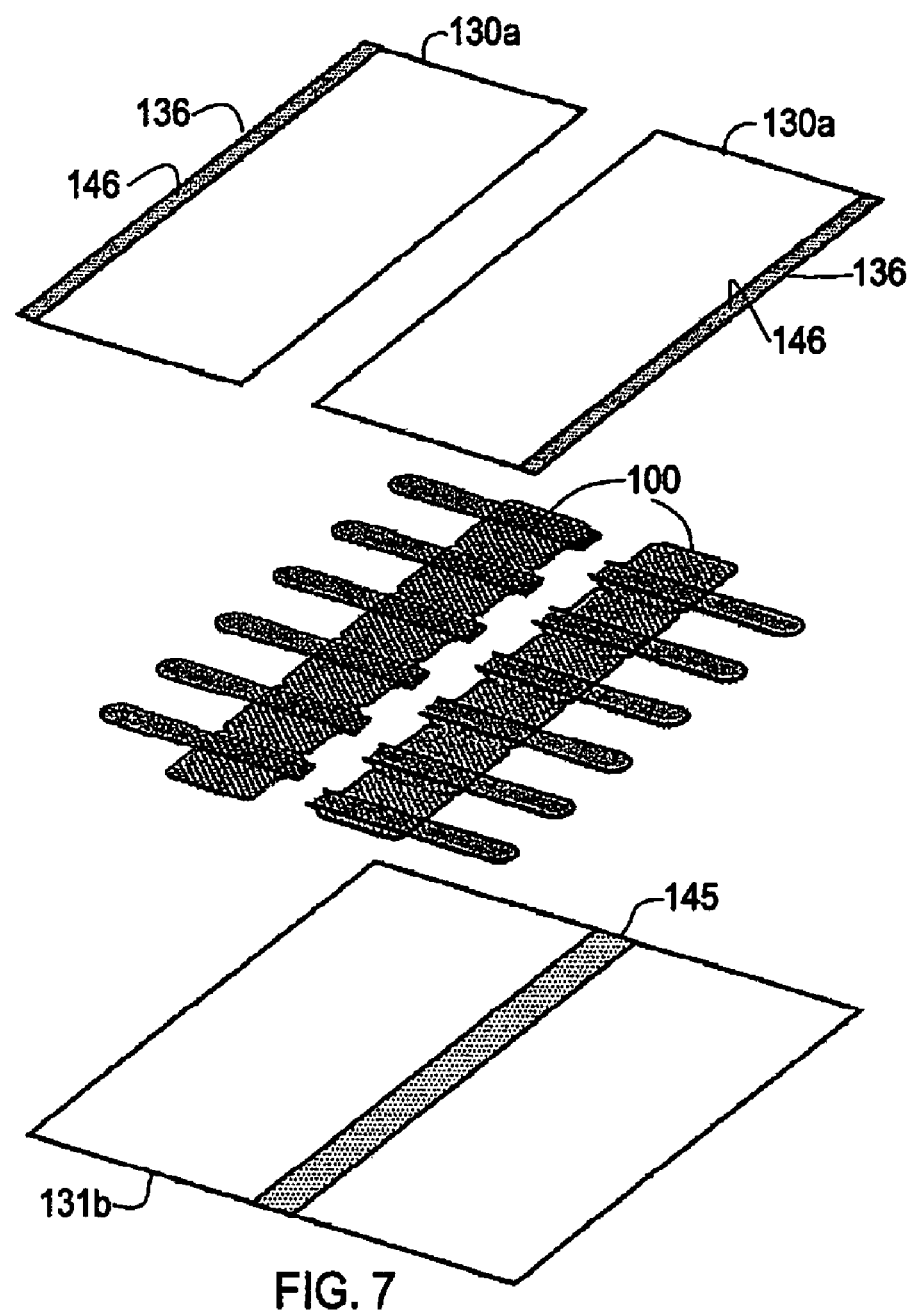
FIG. 7 is an exploded view of the embodiments appearing in FIGS. 6A and 6B.

FIGS. 6A, 6B, and 7 illustrate yet another embodiment which is as described above by way of reference to FIGS. 3A, 3B, and 4, except that two closure devices 100 are placed in opposed relation on a single bottom protective sheet 131b. The units may be placed on opposite sides of indicia 145 running along a center line of the bottom sheet 131b. As best seen in FIG. 6A, the indicia simulates and teaches to the user the relative placement of the devices 100 on either side of a wound such that the opposing bridging links are axially offset to allow for easy closure. Alternately, in the embodiment of FIG. 6B, the hinge tabs 124 may protrude onto the indicia region 145 for ease of visibility of the hinge tabs.

Each unit 100 has a separate upper protective sheet 130a and may be removed from the lower sheet 131b separately using a desired release factor on of the upper sheets 130a. The single bottom sheet 131b may be formed from a single sheet of stock material, or, alternatively, may be formed by securing two sheets 131a together, e.g., using tape, adhesive, or the like.

Figure 8:
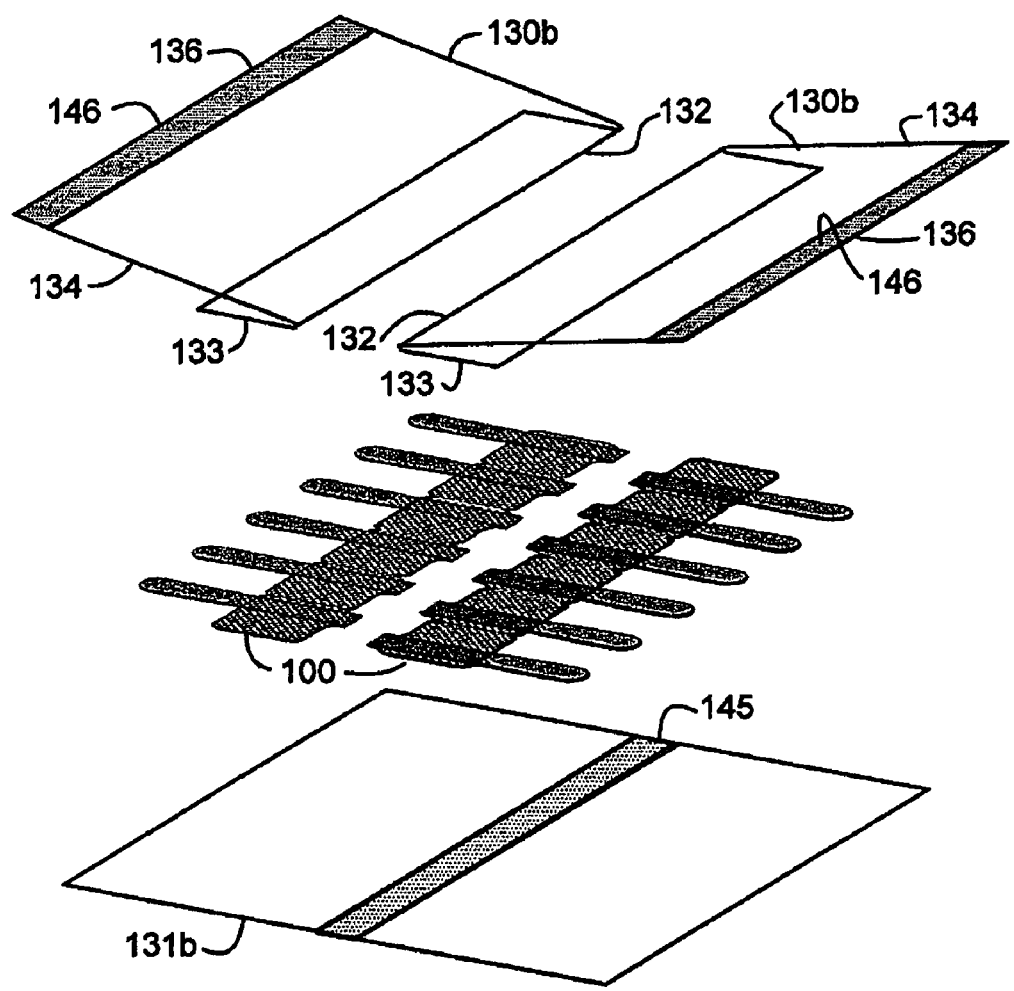
FIG. 8 is an exploded perspective view of a fourth packaged closure configuration.

The further alternative embodiment appearing FIG. 8 differs from that of FIG. 7 in that it includes a pair of upper protective sheets 130b in place of the upper protective sheets 130a, but is otherwise as described above.

Figure 9A:
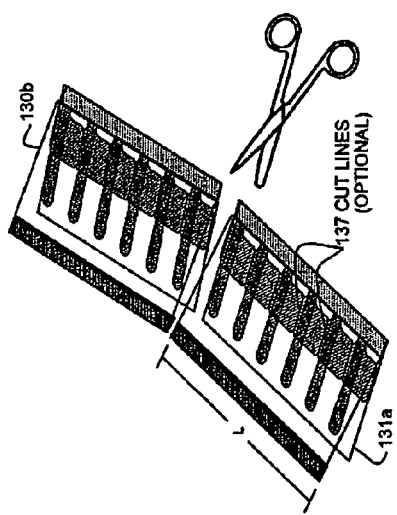
Figure 9B:
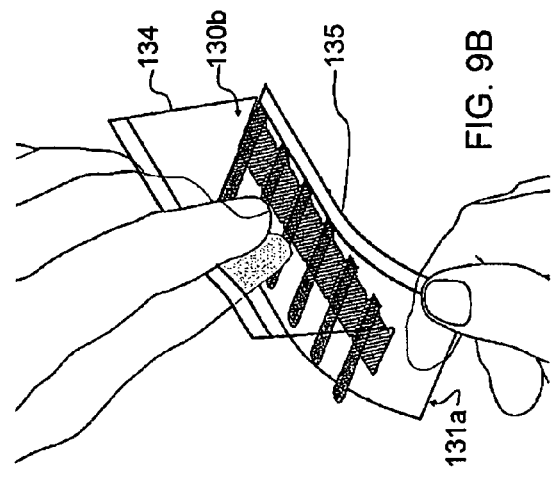

As shown in FIG. 9A, in operation, the wound 121 will be examined and at least one length of the base strip 101, substantially corresponding to the length of the wound 121, will be cut, torn, or separated from the packaged closure device. As shown in FIG. 9B, the flap portion 134 of the upper protective tape 130b is grasped in one hand and the edge 135 of the lower protective tape 131a is grabbed by the other hand. Because of the differential release factors between the upper protective tape 130b and the lower protective tape 131a, the lower tape 131a may be separated from the base strip 101, while the base strip 101 remains attached to the upper protective tape 130b. The flap portion 134 thereby provides a convenient way to hold the wound closure device 100 during placement of the closure device along an edge of wound 121.

As shown in FIG. 9C, the inner edge 106 of the base strip 101 may then be aligned with the edge of the wound 121 and the tabs 124 may be used to gauge the distance from the edge 106 of the base strip 101 to avoid applying an adhesive portion over the wound. Preferably, the gauge distance d may be selected in the range of from about 2 to about 4 mm.

To close the wound, the bridging links 105 are manually pivoted about hinge 124 from their stored position and pulled transverse to the wound lip to close the wound. The closing force is maintained by engaging the adhesive section 108 of the bridging links to the opposite side of the wound.

In the embodiments of FIGS. 3A, 3B, and 4, the process is as substantially as described above. In a preferred embodiment of FIGS. 3A, 3B, and 4, the tabs 124 extend beyond the proximal edge of the upper sheet 130a and the wound closure device 100 and upper sheet 130a may be stripped from the lower sheet 131a to expose the adhesive for application by grasping a tab 124. The upper sheet 130a is then used as a handle for applying the base strip 101 to the area adjacent the wound to be closed.

In FIGS. 7 and 8, the two closure units 100 are removed as detailed above and applied to opposite sides of the wound in sequence prior to securing the bridging links.

Figure 11A:
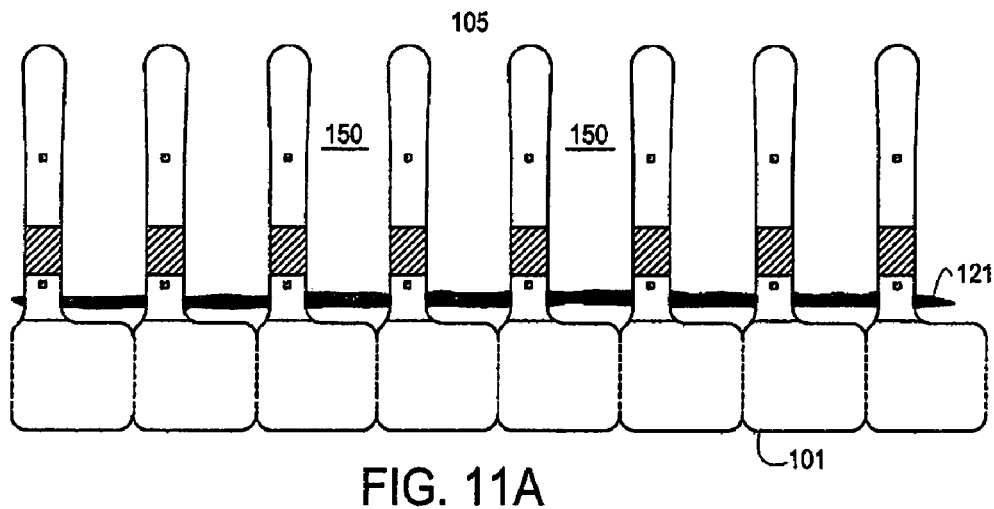
FIGS. 11A and 11B illustrate the wound closure device of FIG. 1 applied on only one side of the wound.
Figure 11B:
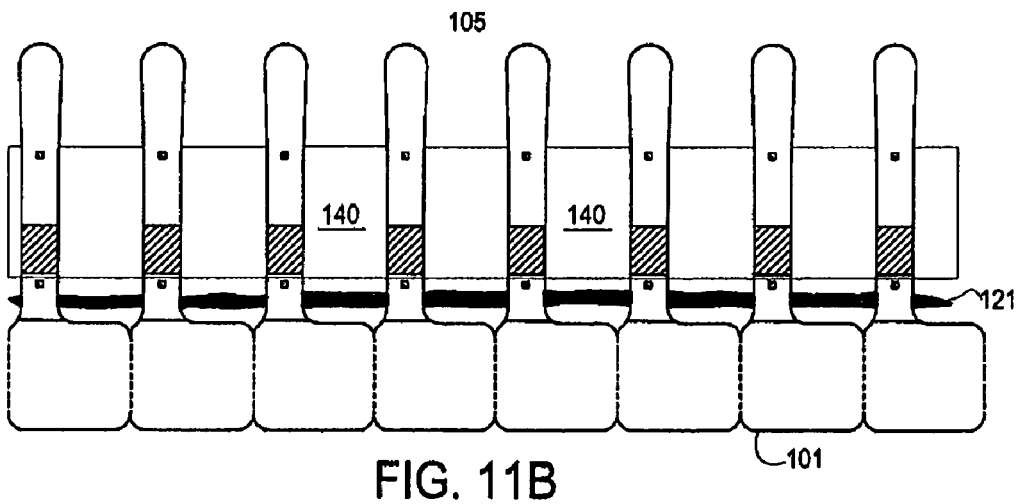

In one embodiment, the adhesive sections 108 of the bridging links 105 are applied directly to the skin 150, see FIG. 11A. In another embodiment, a length of adhesive tape 140 is placed opposite to the cut base strip 101 and the adhesive sections of the bridging links are applied to the upper surface of the adhesive tape 140, see FIG. 11B.

As shown in FIGS. 10A-10C, in another embodiment, approximately equal lengths of base strip 101 are cut to match the length of the wound 121. After sequential removal of the upper and lower protective tapes, the cut lengths are applied to opposite sides of the wound 121. Using a combination of hinge tabs 124 and notches 120, the bridging links 105 of each length of base strip 101 are offset so that they can be extended across the wound in opposing directions. That is, by axially aligning the notches 120 on the opposing base strips 101 applied to opposite sides of the wound 121 to be closed, the bridging links 105 of the two base strips 101 will be axially offset. The bridging links 105 may be then interlaced to engage the top surface of the opposing base strip. In this embodiment the adhesive sections 108 of the bridging links 105 adhesively engage the upper surfaces 114 of the opposing base strip 101.

The present closure device includes many illustrative embodiments, some of which are mentioned below.

Optically Clear Liners

The use of optically clear liners allows the user to intuitively understand how the device works using the see-through capabilities of this substrate. The use of transparent liners is a teaching tool in that it allows the user to visualize the closure strip in its packaged state.

The optically clear liners also provide a way to inspect device for manufacturing defects or other problems.

This see-through capability allows the device to be applied to curved or complicated wounds. Not having to apply the device blindly through opaque materials offers many advantages over other devices.

The see-through capability allows user to clearly identify and not just approximate where the device and the adhesive region are relative to the wound. This allows for greater precision and greater ease in avoiding contact of the wound with the adhesive coated region of the device.

The see-through capability allows the manufacturer to print color coding instructions and other information, logos, trademarks, or other printed matter, on the non-release side of liner.

Red Liner—Clear Color Coded (RCCL)

The Red Coded Clear Liner (RCCL) (see 131a, 131b) helps the user orient the device to the wound. The red line on the release liner simulates the placement of the device on either side of the wound. This design teaches that the relative position of the hinges are staggered or off-set from each other, (across the wound) allowing for easy closure.

The RCCL helps the user identify parts of the device.

The RCCL helps the user determine what steps to take for proper application of device.

The RCCL helps in clarifying application directions (i.e., Step 1. Grasp Hinge and remove device from Red Coded Liner. Step 2. Using Blue Coded Clear Liner as a handle, position device on one side of the wound).

A gray background color may be provided on the RCCL to provide better contrast to see the notches 120 for adjusting and cutting the device to particular wound sizes.

Blue Liner—Clear Color Coded (BCCL)

The Blue Coded Clear Liner (BCCL) provides a mechanism to grasp hinge (adhesive protection cover) for removal of device from Red Coded Clear Liner.

The BCCL provides a see-through capability, providing the user with knowledge of where to cut and where the device is located during the application procedure.

The BCCL provides a means of holding the device (a handle) while applying the device to a straight or even curved wound.

Stiffening and Easy Grip Material (Colored 3M Micropore Tape)

One or more layers of stiffening material provides for an easy grasp of the pulling tabs. With this stiffening material, the pulling tabs are easier to control for precise wound closure.

The pulling tabs may be shaped in an intuitive, pull tab shape to help identify it as a pull tab. The color sets it apart from rest of device.

The stiffening material on the ends of the pull tabs provides a guideline for trimming the pull tabs off the device upon completion of the wound closing procedure.

ORION® Material

In certain embodiments, the closure device 100 may be formed of a conformable non-woven textile-like fabric, e.g., formed of nylon or other synthetic material. The closure device 100 is preferably formed of ORION® spun bond nylon fabric. In particularly preferred embodiments, the closure device 100 is formed of ORION® fabric having a weight in the range of from about 1 to about 2 ounces per square yard and is most preferably in the range of from about 1.8 to about 2.0 ounces per square yard.

The ORION® fabric is breathable, translucent, and high-strength with longitudinal flexibility. The material is formed of nylon and is adaptable to a variety of environments. The flexibility and weight of the material allows it to curve around wounds in a one piece construction. Other devices are inflexible and need to be cut into separately applied segments in order to contour to a curved or other nonlinear or irregular wound.

Base Strip Design

Notches 126 identify where to cut the device 100, so that when it is placed on opposing sides of the wound, the pull tabs/hinges are automatically set up axially staggered. This allows for the optimal amount of space between the pull tabs and optimal space for exudates to pass.

The notches are so positioned so that during manufacturing the device can be cut at any length by a sheeter die. The specific distance from the pull tab to the notches allows ample room (tolerance) for rotary die to function properly.

Rounded edges on each unit and the unique shape of each unit provides for proper adhesion of glue at the corners. Sharp corners are the first place that the device starts separating from the skin. This can be caused by normal wear over time or sharp corners can get suck on clothing and pull off the device.

Hinges

The hinges provide the user with a means of positioning the device at the optimal distance from the wound.

The hinge size provides for optimal breathability and air/exudates exchange.

The hinges provide the user with an intuitive understanding of where the adhesive-free zone is located.

The hinges provide an adhesive-free zone to grip the device during application.

The hinges provide a non-adhesive tab that allows one to remove the device from the red release liner.

Light Tack Adhesive (LTA)

Placement of the light tack adhesive (LTA) 113 is moved toward the rounded end of the pull tabs when the non-folded BCCL liner (130a) is used. This placement of the LTA allows for the removal of the BCCL without going close to the wound edge.

Placement of the LTA 113 is moved toward the hinge area when the folded blue release liner (130b) is used. Placement of the LTA closed to the hinge allows for the removal of the BCCL without going close to the wound edge.

The invention has been described with reference to the preferred embodiments. Modifications and alterations will occur to others upon reading and understanding the preceding detailed description. It is intended that the invention be construed as encompassing all such modifications and alterations insofar as they come within the scope of the appended claims or the equivalents thereof.

Having thus described the preferred embodiments, the invention is now claimed to be:

1. A device for closing a wound, comprising:
   an elongate, flexible base strip having a bottom surface coated with an adhesive to adhere to one side of a wound and a top surface opposite the bottom surface;
   a plurality of bridging links connected to an inner edge of the base strip in axially-spaced relation, said bridging links extending transversely from the inner edge;
   each of said bridging links hingably movable about a hinge section between a first, storage position wherein said bridging links are folded over the top surface of the base strip and a second, extended position wherein said bridging links extend outwardly from said inner edge;
   said bridging links each having a first, engaging surface with an adhesive region thereon to adhere to an opposite side of the wound when the bridging links are in said extended position and a second surface opposite the engaging surface;
   wherein said hinge section is constructed with a fold line on said second surface of said bridging links, said fold line defines a hinge axis in the hinge section, said fold line of said bridging links being positioned outward a distance from said inner edge to define a tab extending outward a predetermined distance from said inner edge when the bridging links are in the first, storage position;
   wherein the adhesive region of the engaging surface of each of said bridging links is positioned outwardly and separately from the hinge section represented by said tab to define an adhesive-free region between the base strip and the adhesive region of the engaging surfaces of said bridging links; and
   said tab may be used as a gauge to maintain an appropriate distance between said inner edge of the base strip and the wound as well as assisting in alignment of the base strip with respect to the wound.

2. The device of claim 1, further comprising:
   a light-tack adhesive on said second surface of the bridging links to releasably secure the second surface of the bridging links to the top surface of the base strip when the bridging links are in the storage position.

3. The device of claim 1, further comprising:
   a lower protective sheet having a first surface treated with a first release agent removably engaging the bottom surface of the base strip; and
   an upper protective sheet having a first surface treated with a second release agent removably engaging the engaging surface of the bridging links, wherein the second release agent is the same as or different than the first release agent.

4. The device of claim 3, wherein the upper protective sheet is selected from:
   a planar sheet of material; and
   a folded sheet of material including a proximal flap engaging the engaging surface of the bridging links and a distal flap portion connected to the proximal flap portion about a fold line to provide a means by which a user can grip the upper protective sheet and exert a removal force thereon.

5. The device of claim 3, further comprising:
   said lower protective sheet having an axially-extending indicia strip, said axially extending indicia strip running generally adjacent and parallel to said inner edge of said base strip.

6. The device of claim 5, further comprising:
   said axially-extending indicia strip having a first edge; and
   said first edge aligned with either: said inner edge; or, said fold lines of said bridging links.

7. The device of claim 6, further comprising:
   said axially-extending indicia strip having a second edge opposite the first edge, said axially-extending indicia strip extending between the first and second edges.

8. The device of claim 7, further comprising:
   said second edge aligned with a peripheral edge of said lower protective sheet.

9. The device of claim 6, wherein said axially-extending indicia strip is visually contrasting with one or both of the material forming the base strip and the material forming the bridging links.

10. The device of claim 3, wherein the lower protective sheet removably engages the bottom surface of the base strip with a first tenacity and the upper protective sheet removably engages the engaging surface of the bridging links with a second tenacity which is greater than the first tenacity.

11. The device of claim 1, wherein the base strip is formed of a conformable, non-woven material.

12. The device of claim 1, wherein the base strip is formed of a spun bonded nylon material.

13. The device of claim 1, wherein said distance between said fold line of said bridging links and said inner edge defining said tab when the bridging links are in the first, storage position is configured to be approximately equal to a desired distance between said inner edge and an edge of the wound.

14. The device of claim 1, further comprising one or more layers of material laminated to one or both of:
   the first, engaging surface of the bridging links; and a second surface of the bridging links opposite the first, engaging surface.

15. The device of claim 14, further comprising:
said one or more layers of material extending from a distal end of said bridging links to a position intermediate said distal end and said fold line.

16. The device of claim 15, wherein the one or more layers of material are selected from any one or more of: micropore tape, a textured material to facilitate gripping said bridging links, a stiffening material, and a material having a contrasting visual appearance with a material forming the bridging links.

17. The device of claim 15, further comprising:
said one or more layers of material extending between the distal end of said bridging links to a position defining a preferential cut line for trimming the bridging links after application of the device to the wound; and
at least one of said one or more layers of material being visually contrasting with respect to said bridging links to provide a visual indication of said preferential cut line.

18. The device of claim 1, further comprising:
at least one notch formed in said inner edge of the base strip, said at least one notch being positioned between each adjacent pair of bridging links offset from a centered position between adjacent pair of bridging links.

19. A device for closing a wound, comprising:
a first closure strip removably attached to a first surface of a lower protective sheet, said first surface treated with a release agent;
a second closure strip removably attached to the first surface of the lower protective sheet, the first and second closure strips in aligned, facing relation;
each of said first and second closure strips including an elongate, flexible base strip having a bottom surface coated with an adhesive to adhere to a first side of a wound and a top surface opposite the bottom surface;
each of said first and second closure strips including a plurality of bridging links connected to an inner edge of the base strip in axially-spaced relation, said bridging links extending transversely from the inner edge;
each of said bridging links hingably movable about a fold line between a first, storage position wherein said bridging links are folded over the top surface of the base strip and a second, extended position wherein said bridging links extend outwardly from said inner edge;
said bridging links each having a first, engaging surface having an adhesive region thereon to adhere to the opposite side of the wound when the bridging links are in said extended position and a second surface opposite the engaging surface;
said fold line on said second surface of said bridging links transversely spaced apart a distance from said inner edge and a transverse extent of each bridging link extending between the inner edge and the fold line defining a tab when the bridging links are in the first, storage position;
between each adjacent pair of bridging links, a notch formed in said inner edge, said notch being positioned between each adjacent pair of bridging links offset from centered position between adjacent pair of bridging links such that when said first closure strip is positioned on a first side of the wound and said second closure strip is positioned in facing relation on a second side of the wound opposite the first side and the notches of said first closure strip are in axial alignment with notches of said second closure strip, the bridging links of said wound closure device will be axially offset from bridging links of said second closure strip;
one or more layers of material laminated to one or both of: the first, engaging surface of the bridging links; and a second surface of the bridging links opposite the first, engaging surface;
wherein the adhesive region of the engaging surface of each of said bridging links is positioned outwardly and separately from the hinge section represented by a tab to define an adhesive-free region between the base strip and the adhesive region of the engaging surface of said bridging links; and
said tab may be used as a gauge to maintain an appropriate distance between said inner edge of the base strip and the wound as well as assisting in alignment of the base strip with respect to the wound.

* * * * *